United States Patent
Chen et al.

(10) Patent No.: US 10,473,610 B2
(45) Date of Patent: Nov. 12, 2019

(54) PLANAR AMMONIA SELECTIVE SENSING ELECTRODE AND MANUFACTURING METHOD THEREOF

(71) Applicant: Akubic (Cayman) Limited, Grand Cayman (KY)

(72) Inventors: Kuan-Jung Chen, Taipei (TW); Shih-Hao Ko, Taipei (TW); Chih-Yung Tseng, Taipei (TW); Hsiao-Han Yu, Taipei (TW)

(73) Assignee: AKUBIC (CAYMAN) LIMITED, Grand Cayman (KY)

( * ) Notice: Subject to any disclaimer, the term of this patent is extended or adjusted under 35 U.S.C. 154(b) by 90 days.

(21) Appl. No.: 15/641,940

(22) Filed: Jul. 5, 2017

(65) Prior Publication Data
US 2018/0106753 A1  Apr. 19, 2018

Related U.S. Application Data

(60) Provisional application No. 62/408,924, filed on Oct. 17, 2016.

(30) Foreign Application Priority Data

May 25, 2017 (CN) .......................... 2017 1 0377336

(51) Int. Cl.
*G01N 27/333* (2006.01)
*G01N 27/407* (2006.01)
(Continued)

(52) U.S. Cl.
CPC ....... *G01N 27/333* (2013.01); *G01N 27/3335* (2013.01); *G01N 27/4072* (2013.01);
(Continued)

(58) Field of Classification Search
CPC ...... G01N 33/18; G01N 31/221; G01N 27/27; G01N 27/4166; G01N 33/1813;
(Continued)

(56) References Cited

U.S. PATENT DOCUMENTS 4,713,165 A * 12/1987 Conover ................ C12Q 1/001
204/403.05
4,872,966 A * 10/1989 Kotani .................. G01N 27/333
204/414
(Continued)

FOREIGN PATENT DOCUMENTS

CN   103592162 A   2/2014
CN   104155355 A   11/2014
(Continued)

*Primary Examiner* — Freddie Kirkland, III
(74) *Attorney, Agent, or Firm* — Kirton McConkie; Evan R. Witt (57) ABSTRACT

A planar ammonia selective sensing electrode for water quality monitoring and a manufacturing method of the sensing electrode are provided. The sensing electrode includes an insulating base plate, an electric-conductive layer, an ammonium ion sensing layer, a hydroxide ion sensing layer, and an electrolyte layer. The electric-conductive layer is disposed on the planar surface of the insulating base plate. The electric-conductive layer includes a first conductive part and a second conductive part. The first conductive part and the second conductive part are insulated and apart from each other, and configured to form a first reaction zone and a second reaction zone, respectively. The ammonium ion sensing layer is disposed on the first reaction zone. The hydroxide ion sensing layer is disposed on the second reaction zone. The electrolyte layer is disposed on and covers the ammonium ion sensing layer and the hydroxide ion sensing layer.

17 Claims, 4 Drawing Sheets

(51) Int. Cl.
*G01N 33/18* (2006.01)
*G01N 27/12* (2006.01)
*C01C 1/02* (2006.01)
*C02F 1/58* (2006.01)

(52) U.S. Cl.
CPC ......... *G01N 33/18* (2013.01); *G01N 33/1813* (2013.01); *C01C 1/024* (2013.01); *C02F 1/586* (2013.01); *G01N 27/126* (2013.01)

(58) Field of Classification Search
CPC ............ G01N 27/333; G01N 27/3335; G01N 27/4072; G01N 27/126; C02F 2209/06; C02F 1/586; C01C 1/024
USPC .................................................. 204/400, 415
See application file for complete search history.

(56) References Cited

U.S. PATENT DOCUMENTS

| | | | | |
|---|---|---|---|---|
| 5,234,568 A * | 8/1993 | Tomita | ................ | G01N 27/307 |
| | | | | 204/406 |
| 5,248,403 A * | 9/1993 | Tomita | ................ | G01N 27/307 |
| | | | | 204/409 |
| 5,660,790 A * | 8/1997 | Lawrence | ............ | G01N 31/221 |
| | | | | 422/426 |
| 6,666,963 B1 | 12/2003 | Peng et al. | | |
| 6,761,817 B2 * | 7/2004 | Connery | ............. | G01N 27/404 |
| | | | | 204/401 |
| 6,964,734 B2 * | 11/2005 | Cha | ..................... | G01N 27/301 |
| | | | | 204/435 |
| 7,790,113 B2 * | 9/2010 | Putnam | ................ | G01N 31/221 |
| | | | | 422/82.01 |
| 8,202,503 B2 * | 6/2012 | Putnam | ................ | G01N 31/221 |
| | | | | 423/237 |
| 9,063,071 B2 * | 6/2015 | Iwamoto | ................. | G01N 27/27 |
| 9,151,727 B2 * | 10/2015 | Iwamoto | ............... | G01N 27/333 |
| 9,377,429 B2 * | 6/2016 | Iwamoto | ................. | G01N 27/28 |
| 10,031,099 B2 | 7/2018 | Lauks et al. | | |
| 10,139,362 B2 * | 11/2018 | Ohgami | ............ | G01N 27/3272 |
| 2001/0032785 A1 | 10/2001 | Cha et al. | | |
| 2003/0111358 A1 | 6/2003 | Connery | | |
| 2005/0252790 A1 | 11/2005 | Dobson et al. | | |
| 2007/0256944 A1 * | 11/2007 | Lin | ...................... | G01N 27/404 |
| | | | | 205/782 |
| 2010/0326845 A1 * | 12/2010 | Lin | ...................... | G01N 27/404 |
| | | | | 205/785.5 |
| 2013/0168247 A1 * | 7/2013 | Iwamoto | ............... | G01N 27/333 |
| | | | | 204/417 |
| 2014/0209485 A1 * | 7/2014 | Ohgami | ............... | G01N 27/333 |
| | | | | 205/789 |
| 2016/0209346 A1 * | 7/2016 | Brondum | ............... | G01N 27/07 |
| 2018/0105941 A1 * | 4/2018 | Chen | ........................ | C25B 3/10 |
| 2018/0275086 A1 * | 9/2018 | Parat | .................... | G01N 27/308 |
| 2019/0025273 A1 * | 1/2019 | Brondum | ................ | C02F 1/008 |

FOREIGN PATENT DOCUMENTS

| | | |
|---|---|---|
| TW | 200739064 A | 10/2007 |
| TW | 201538973 A | 10/2015 |
| WO | 2008031091 A2 | 3/2008 |
| WO | 2013081443 A1 | 6/2013 |

* cited by examiner

PLANAR AMMONIA SELECTIVE SENSING ELECTRODE AND MANUFACTURING METHOD THEREOF

CROSS-REFERENCE TO RELATED APPLICATION

This application claims the benefit of U.S. Provisional Application No. 62/408,924 filed on Oct. 17, 2016, and entitled "ELECTROCHEMICAL SENSING DEVICE FOR WATER QUALITY MONITORING PLANAR SENSING ELECTRODES AND FABRICATING METHOD THEREOF". This application claims priority to China Patent Application No. 201710377336.3 filed on May 25, 2017. The entire contents of the above-mentioned applications are incorporated herein by reference for all purposes.

FIELD OF THE INVENTIO

The present invention relates to a sensing electrode for water quality monitoring, and more particularly to a planar ammonia selective sensing electrode and a manufacturing method thereof.

BACKGROUND OF THE INVENTION

For a conventional water quality monitoring, it takes a lot of time and manpower to sample and analyze, and the problems of the ineffective wastewater treatment or the abnormal quality of the treated water cannot be reported efficiently and immediately, so that the quality of the river's receiving water is affected by the discharged wastewater. In order to meet the actual demand, the water quality monitoring device should be able to analyze the real-time water quality to effectively monitor the effectiveness of the water treatment and the changing conditions of the water quality, thereby improving the corresponding operating procedures of handling process. On the other hand, while the requirement for recycling water is increased, the requirement of the water quality monitoring device with the on-site monitoring ability is also increased significantly.

However, the conventional water quality monitoring device is provided with a glass electrode as its ion sensing electrode. Although the glass electrode can be used to measure the ion concentration in the water stably, it has a complex structure, costs a lot, and is not conducive to miniaturization. In addition, due to the structural limitations of the glass electrode and the reference electrode in the water quality monitoring device, the sensing sensitivity thereof cannot be improved.

Therefore, there is a need of providing a planar ammonia selective sensing electrode and a manufacturing method thereof for water quality monitoring to meet the above requirements and solve the above problems.

SUMMARY OF THE INVENTION

An object of the present invention is to provide a planar ammonia selective sensing electrode and a manufacturing method thereof. The planar ammonium ion sensing layer and the planar hydroxide ion sensing layer are disposed on an electric-conductive by a drop-coating method, a sputtering method, an electrodeposition method or a screen-printing thick-film technique, so as to improve the accuracy and reduce the volume of the sensing electrode. At the same time, the planar ammonia selective sensing electrode is provided with the high selectivity and the high sensitivity to be applied in the fields of the medicine, the biochemistry, the chemistry, the agriculture, the environmental and others. For example, it can be applied to monitor the variation of the ammonia and nitrogen concentrations during the planting process of hydroponic plants, the variation of the ammonia and nitrogen concentrations of the human sweat, the water quality of the aquaculture, or the specific biological indicators (e.g. creatinine) by means of combining the specific enzymes.

Another object of the present invention is to provide a planar ammonia selective sensing electrode and a manufacturing method thereof. The structure is compact, the manufacturing process is simplified, and the cost is reduced, so as to facilitate to achieve the purpose of providing disposable sensing electrodes.

In accordance with an aspect of the present invention, a planar ammonia selective sensing electrode is provided. The planar ammonia selective sensing electrode includes an insulating base plate, an electric-conductive layer, an ammonium ion sensing layer, a hydroxide ion sensing layer and an electrolyte layer. The insulating base plate includes at least one planar surface. The electric-conductive layer is disposed on the planar surface of the insulating base plate. The electric-conductive layer includes at least one first conductive part and at least one second conductive part. The first conductive part and the second conductive part are insulated and apart from each other, and further configured to form a first reaction zone and a second reaction zone, respectively. The ammonium ion sensing layer is disposed on the first reaction zone of the first conductive part. The hydroxide ion sensing layer is disposed on the second reaction zone of the second conductive part. The electrolyte layer is disposed on and covers the ammonium ion sensing layer and the hydroxide ion sensing layer.

In accordance with another aspect of the present invention, a manufacturing method of a planar ammonia selective sensing electrode is provided. The manufacturing method includes steps of: (a) providing an insulating base plate including at least one planar surface, and forming an electric-conductive layer on the at least one planar surface of the insulating base plate, wherein the electric-conductive layer includes at least one first conductive part and at least one second conductive part, and the first conductive part and the second conductive part are insulated and apart from each other and configured to form a first reaction zone and a second reaction zone, respectively; (b) forming an ammonium ion sensing layer on the first reaction zone and a hydroxide ion sensing layer on the second reaction zone, respectively; and (c) forming an electrolyte layer to cover over the ammonium ion sensing layer and the hydroxide ion sensing layer.

The above contents of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

The present invention provides a planar ammonia selective sensing electrode. The planar ammonia selective sensing electrode includes an insulating base plate, an electric-conductive layer, an ammonium ion sensing layer, a hydroxide ion sensing layer and an electrolyte layer. In the present invention, the hydroxide ion sensing layer can be for example but not limited to a potential of hydrogen sensing layer or a pH sensing layer. The electric-conductive layer is disposed on the planar surface of the insulating base plate. The electric-conductive layer includes at least one first conductive part and at least one second conductive part. The first conductive part and the second conductive part are insulated and apart from each other, and further configured to form a first reaction zone and a second reaction zone, respectively. The ammonium ion sensing layer is disposed on the first reaction zone of the first conductive part. The hydroxide ion sensing layer is disposed on the second reaction zone of the second conductive part. The electrolyte layer is disposed on and covers the ammonium ion sensing layer and the hydroxide ion sensing layer. The planar ammonium ion sensing layer and the planar hydroxide ion sensing layer are disposed on the electric-conductive by a drop-coating method, a sputtering method, an electrodeposition method or a screen-printing thick-film technique. Moreover, without the loss of the accuracy, the volume of the planar ammonia selective sensing electrode is greatly reduced, and the planar ammonia selective sensing electrode has high selectivity and high sensitivity.

Figure 1:
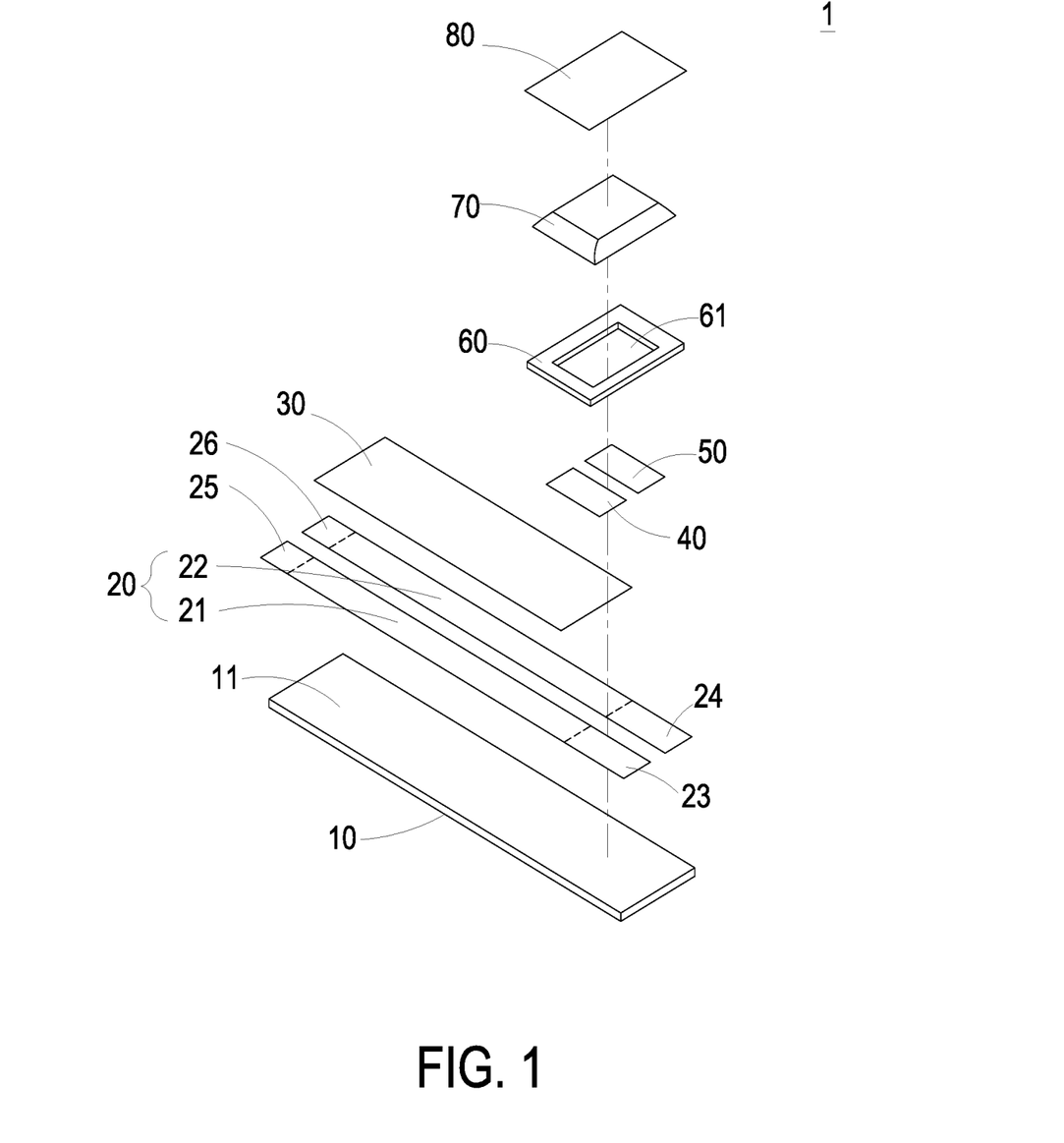
FIG. 1. It is an exploded view illustrating a planar ammonia selective sensing electrode according to a preferred embodiment of the present invention.

FIG. 1 is an exploded view illustrating a planar ammonia selective sensing electrode according to a preferred embodiment of the present invention. As shown in FIG. 1, the planar ammonia selective sensing electrode (hereinafter referred as the sensing electrode) 1 includes an insulating base plate 10, an electric-conductive layer 20, an insulating and waterproof layer 30, an ammonium ion sensing layer 40, a pH sensing layer 50, a pad 60, an electrolyte layer 70 and a gas diffusion layer 80. The insulating base plate 10 includes at least one planar surface 11. The electric-conductive layer 20 includes a first conductive part 21 and a second conductive part 22 disposed on the planar surface 11 of the insulating base plate 10, respectively, and insulated and apart from each other. In the embodiment, the first conductive layer 21 and the second conductive layer 22 are preferably disposed on the same planar surface 11. The first conductive part 21 and the second conductive part 22 include a first reaction zone 23 and a second reaction zone 24, respectively. The insulating and waterproof layer 30 is disposed on the electric-conductive layer 20 and partially covers the first conductive part 21 and the second conductive part 22, and thus a portion of the first conductive part 21 and a portion of the second conductive part 22 are exposed from the insulating and waterproof layer 30 and configured as the first reaction zone 23 and the second reaction zone 24, respectively. In the embodiment, the first reaction zone 23 of the first conductive part 21 and the second reaction zone 24 of the second conductive part 22 are disposed nearby with a gap so as to facilitate the miniaturization of the entire structure. Preferably, the first reaction zone 23 and the second reaction zone 24 are located at the ends of the first conductive part 21 and the second conductive part 22, respectively. The ammonium ion sensing layer 40 and the pH sensing layer 50 are disposed on the first conductive part 21 and the second conductive part 22, respectively, and uncovered by the insulating and waterproof layer 30. Namely, each of them is disposed on the first reaction zone 23 and the second reaction zone 24, respectively. In other words, the insulating and waterproof layer 30, the ammonium ion sensing layer 40 and the pH sensing layer 50 cover on the electric-conductive layer 20 together. In the embodiment, the insulating and waterproof layer 30, the ammonium ion sensing layer 40 and the pH sensing layer 50 can be for example but not limited to be constructed on the same planar surface. Preferably, not only the first reaction zone 23 and the second reaction zone 24 are located at the ends of the first conductive part 21 and the second conductive part 22, respectively, but also a working electrode connection zone 25 and a counter electrode connection zone 26 are disposed on the first conductive part 21 and the second conductive part 22, respectively, and located at the other ends opposite to the ends where the first reaction zone 23 and the second reaction zone 24 located at. Besides, the electrolyte layer 70 is disposed on the ammonium ion sensing layer 40 and the pH sensing layer 50 and covers on the ammonium ion sensing layer 40 and the pH sensing layer 50 at the same time. In the embodiment, the sensing electrode 1 further includes a pad 60 having an opening 61. The pad 60 is disposed around the ammonium ion sensing layer 40, the pH sensing layer 50 and the electrolyte layer 70. Consequently, the electrolyte layer 70 passes through the opening 61, is accommodated in the interior of the opening 61, and contacts with the ammonium ion sensing layer 40 and the pH sensing layer 50. In addition, the sensing electrode 1 further includes a gas diffusion layer 80 disposed on the electrolyte layer 70 and attached to the pad 60, so as to hold the electrolyte layer 70 among the gas diffusion layer 80, the ammonium ion sensing layer 40 and the pH sensing layer 50. Thus, the targeted sensing ions can be transmitted from the gas diffusion layer 80 through the electrolyte layer 70 to the ammonium ion sensing layer 40 and the pH sensing layer 50, respectively.

In the embodiment, the targeted sensing ions for the ammonium ion sensing layer 40 and the pH sensing layer 50 are the ammonium ion ($NH_4^+$) and the hydroxide ion ($OH^-$), respectively. Since an ammonia deprotonates the water to give the ammonium ion ($NH_4^+$) and the hydroxide ion ($OH^-$), the reaction equation is shown in the following equation (1). The ammonia ($NH_3$) molecules of the sampled water diffuse into the electrolyte layer 70 through the gas diffusion layer 80 to change the concentrations of the ammonium ion ($NH_4^+$) and the hydroxide ion ($OH^-$) therein, and then the ammonium ion ($NH_4^+$) and the hydroxide ion ($OH^-$) are transmitted to the ammonium ion sensing layer 40 and the pH sensing layer 50, respectively. The ammonium ion ($NH_4^+$) is reacted with the ammonium ion sensing layer 40 to generate the variation of the electrochemical membrane voltage. While the concentration of the ammonium ion ($NH_4^+$) is higher in the aqueous solution, the generated membrane voltage is higher at the ammonium ion sensing layer 40. On the other hand, as ammonia is dissolved in the aqueous solution and hydroxide ions (OH⁻) are generated, an alkaline change in the aqueous solution results. At this time, the sensing voltage of the hydroxide ion (OH⁻) at the pH sensing layer 50 has a negative growth. Namely, while the aqueous solution is getting more alkaline, the voltage of the hydroxide ions (OH⁻) sensed by the pH sensing layer 50 is lower. Therefore, when the ammonia exists in the aqueous solution, the signals sensed at the ammonium ion sensing layer 40 and the pH sensing layer 50 can be added together, and the sensing electrode 1 of the present invention can greatly enhance the sensitivity of ammonia concentration sensing by the conventional electrochemical measure.

$$NH_3 + H_2O \rightleftharpoons NH_3 \cdot H_2O \rightleftharpoons NH_4^+ + OH^- \qquad (1)$$

Figure 2:
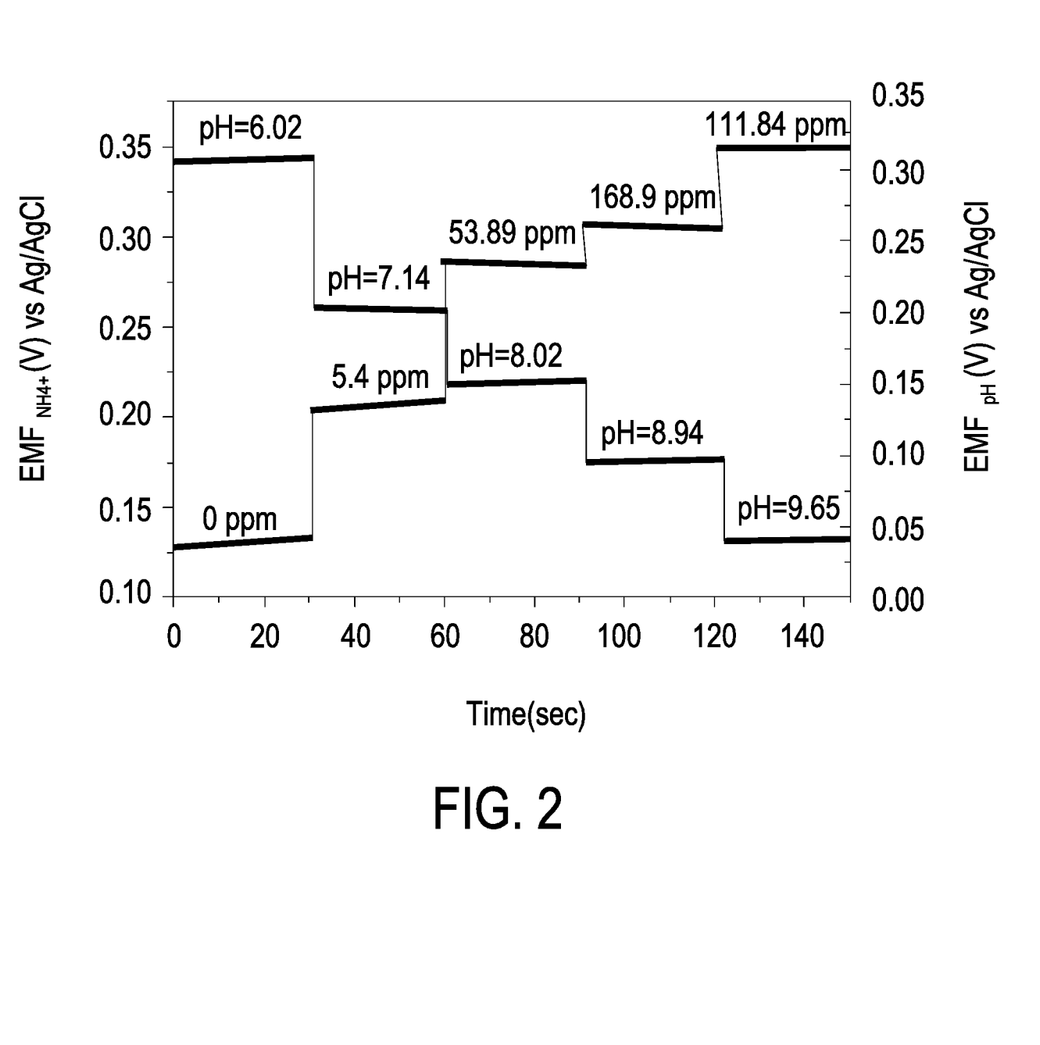
FIG. 2 shows an exemplary sensing voltage response curve of the planar ammonia selective sensing electrode according to the present invention.
Figure 3:
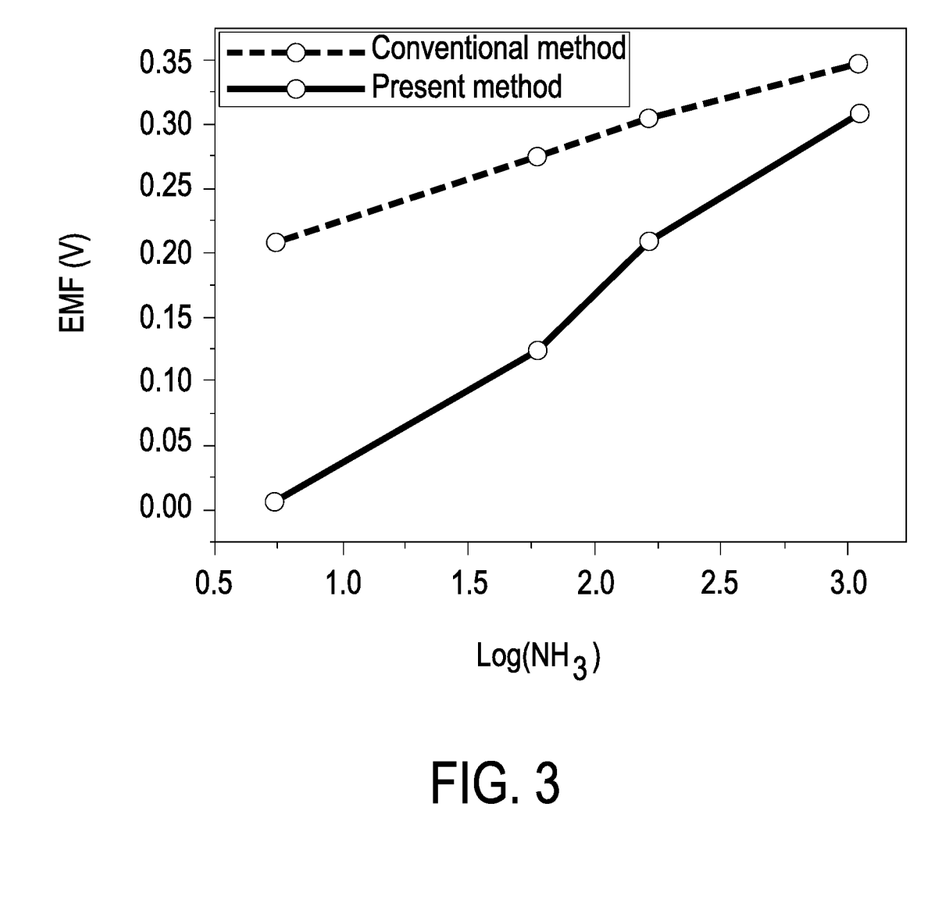
FIG. 3 shows the relationship between the sensing voltage and the ammonia concentration sensed by the planar ammonia selective sensing electrode of the present invention and by the conventional ammonia sensing electrode.

FIG. 2 shows an exemplary sensing voltage response curve of the planar ammonia selective sensing electrode according to the present invention. FIG. 3 shows the relationship between the sensing voltage and the ammonia concentration sensed by the planar ammonia selective sensing electrode of the present invention and by the conventional ammonia sensing electrode. As shown in FIGS. 2 and 3, while the ammonia/ammonium concentration of the aqueous solution gets increasing, the membrane voltage is obtained relative to the silver/silver chloride reference electrode merely according to the conventional measure method. Namely, the ammonia/ammonium concentration sensing voltage is presented as $E_{NH4+} = E_{Working(NH4+)} - E_{Reference}$. While the ammonia/ammonium concentration is getting higher, the sensing voltage of the ammonia/ammonium concentration relative to the silver/silver chloride reference electrode is higher, and it meets the variations in the slope of the electrochemical Nernst equation of 59.2±2 mV/(decade). However, in the embodiment, since the variation of pH value in the aqueous solution is also associated to calculate simultaneously, the pH sensing voltage relative to the silver/silver chloride reference electrode is presented as $E_{pH} = E_{Working(pH)} - E_{Reference}$. While the aqueous solution is influenced by the dissolved ammonia to generate the reaction as shown in the equation (1), it results in increasing the pH value of the aqueous solution and the pH sensing voltage $E_{pH}$ becomes lower. Therefore, in the embodiment, the sensing method of the sensing electrode 1 is performed by the difference between the ammonia/ammonium-concentration sensing voltage $E_{NH4+}$ and the pH sensing voltage $E_{pH}$, and presented as $E_{NH4+} - E_{pH} = E_{Working(NH4+)} - E_{Working(pH)}$, so that the sensitivity of planar ammonia selective sensing electrode 1 is improved and the result meets the variations in the slope of 132±3 mV/(decade), which is higher than the sensitivity of the above conventional sensing electrode in the slope of 59.2±2 mV/(decade) a lot, as shown in FIG. 3 and the following Table 1.

TABLE 1

Comparison of the planar ammonia selective sensing electrode according to the present invention and the conventional ammonia sensing electrode

|  | the present sensing electrode | the conventional sensing electrode |
|---|---|---|
| linearity range | 0.01-1400 ppm | 0.01-1400 ppm |
| linearity | $R^2 = 0.9901$ | $R^2 = 0.9954$ |
| sensitivity | 132 mV/decade | 59.2 mV/decade |

Figure 4:
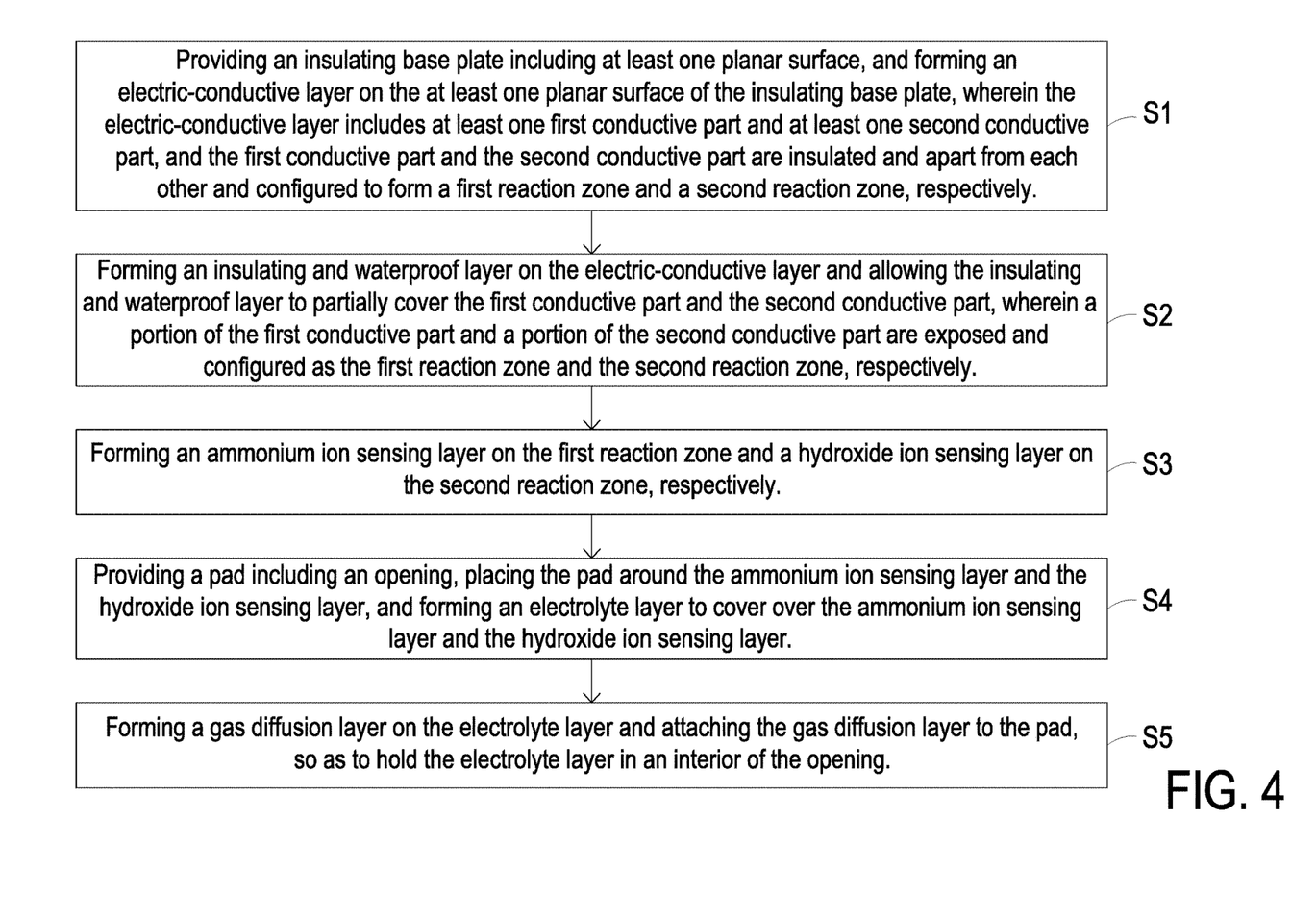
FIG. 4 is a flow chart illustrating a manufacturing method of the planar ammonia selective sensing electrode according to the present invention.

On the other hand, according to the planar ammonia selective sensing electrode described in the above embodiments, a manufacturing method of a planar ammonia selective sensing electrode is provided. FIG. 4 is a flow chart illustrating a manufacturing method of the planar ammonia selective sensing electrode according to the present invention. Please refer to FIGS. 1 and 4. Firstly, at the step S1, an insulating base plate 10 including at least one planar surface 11 is provided, and an electric-conductive layer 20 is formed on the at least one planar surface 11 of the insulating base plate 10. The electric-conductive layer 20 includes a first conductive part 21 and a second conductive part 22 disposed on the planar surface 11 of the insulating base plate 10, respectively, by for example but not limited to a screen-printing or a sputtering technique, and the first conductive part 21 and the second conductive part 22 are insulated and apart from each other. The first conductive part 21 and the second conductive part 22 include a first reaction zone 23 and a second reaction zone 24, respectively. Then, at the step S2, an insulating and waterproof layer 30 is formed on the electric-conductive layer 20 to partially cover the first conductive part 21 and the second conductive part 22, and thus a portion of the first conductive part 21 and a portion of the second conductive part 22 are exposed from the insulating and waterproof layer 30 respectively. The exposed parts of the first conductive part 21 and the second conductive part 22 from the insulating and waterproof layer 30 are configured as the first reaction zone 23 and the second reaction zone 24, respectively. In the embodiment, the insulating and waterproof layer 30 is formed by for example but not limited to a screen-printing or a chemical vapor deposition (CVD) technique to partially cover on the electric-conductive layer 20, and thus the uncovered parts of the electric-conductive layer 20 are configured as the first reaction zone 23 of the first conductive part 21 and the second reaction zone 24 of the second conductive part 22, respectively. In the embodiment, the first reaction zone 23 of the first conductive part 21 and the second reaction zone 24 of the second conductive part 22 are disposed nearby with a gap so as to facilitate the miniaturization of the entire structure. In an embodiment, the first reaction zone 23 and the second reaction zone 24 exposed to be formed on the ends of the first conductive part 21 and the second conductive part 22, respectively. The other ends opposite to the ends with the first reaction zone 23 and the second reaction zone 24 are also exposed from the insulating and waterproof layer 30. They are configured to form a working electrode connection zone 25 and a counter electrode connection zone 26, respectively for constructing a sensing circuit, but it is not a necessary technical feature to limit the present invention, and not redundantly described herein. Then, at the step S3, the ammonium ion sensing layer 40 and the pH sensing layer 50 are formed on the first reaction zone 23 of the first conductive part 21 and the second reaction zone 24 of the second conductive part 22, respectively. In the embodiment, the insulating and waterproof layer 30, the ammonium ion sensing layer 40 and the pH sensing layer 50 are constructed together to cover on the electric-conductive layer 20. The forming sequences of the insulating and waterproof layer 30, the ammonium ion sensing layer 40 and the pH sensing layer 50 are not limited and can be adjusted according to the practical requirements. The details are not redundantly described herein. Afterward, at the step S4, the electrolyte layer 70 is formed to cover the ammonium ion sensing layer 40 and the pH sensing layer 50. In the embodiment, the accommodation space of the electrolyte layer 70 is further defined by an opening 61 of a pad 60. The pad 60 is disposed around the ammonium ion sensing layer 40, the pH sensing layer 50 and the electrolyte layer 70. Consequently, the electrolyte layer 70 passes through the opening 61, is accommodated in the interior of the opening 61, and contacts with the ammonium ion sensing layer 40 and the pH sensing layer 50. The pad 60 can be formed by the materials for example but not limited to the polyethylene terephthalate (PET). In addition, the electrolyte layer 70 can be constructed by filling with for example but not limited to 0.01 M tris (hydroxymethyl) aminomethane (Tris) aqueous solution in the accommodation space defined by the opening 61 of the pad 60. Finally, at the step S5, a gas diffusion layer 80 is formed on the electrolyte layer 70 and attached to the pad 60, so as to hold the electrolyte layer 70 among the gas diffusion layer 80, the ammonium ion sensing layer 40 and the pH sensing layer 50. Namely, the electrolyte layer 70 is accommodated in the accommodation space defined by the opening 61 of the pad 60. In the embodiment, the gas diffusion layer 80 can be for example but not limited to a 10 μm-thickness polytetrafluoroethylene (PTFE) gas diffusion layer.

In the embodiment, the electric-conductive layer 20 is formed on the planar surface 11 of the insulating base plate 10 by for example but not limited to a screen-printing or a sputtering technique. The first reaction zone 23 of the first conductive part 21 and the second reaction zone 24 of the second conductive part 22 are covered by the ammonium ion sensing layer 40 and the pH sensing layer 50, respectively, and regarded as the ammonium ions ($NH_4^+$) reaction zone and the hydroxide ion ($OH^-$) reaction zone, while the remaining parts are covered and protected by an insulating and waterproof layer 30. In an embodiment, the first conductive part 21 and the second conductive part 22 further includes a working connection zone 25 and a counter electrode connection zone 26, respectively, located at the other ends opposite to the ends of the first reaction zone 23 and the second reaction zone 24 covered by the ammonium ion sensing layer 40 and the pH sensing layer 50, respectively, and connected to the connection wires (not shown) for forming a sensing circuit. In the embodiment, the electric-conductive layer 20 can be for example but not limited to a sputtering metal film, and its material is selected from a screen-printing silver-carbon conductive mixing slurry, a gold paste, a palladium paste, a silver paste, a conductive carbon slurry, a gold, a palladium, a platinum, a gold-palladium alloy, a silver or the combinations thereof. The insulating base plate 10 is formed by for example but not limited to a PET or a ceramic substrate. In an embodiment, the electric-conductive layer 20 is formed on the insulating base plate 10 by a printing method and then dried at for example 60° C. to 140° C.

In the embodiment, the first reaction zone 23 of the first conductive part 21 of the electric-conductive layer 20 is covered by the ammonium ion sensing layer 40, and the second reaction zone 24 of the second conductive part 22 is covered by the pH sensing layer 50. The first reaction zone 23 and the second reaction zone 24 are configured to form the ammonium ion ($NH_4^+$) reaction zone and the hydroxide ion ($OH^-$) reaction zone, respectively, so as to transmit the voltage variations of the electrochemical membrane voltage generated by the ammonium ion sensing layer 40 and the pH sensing layer 50, respectively, and transmit the electric signal through the working electrode connection zone 25 of the first conductive part 21 and the counter electrode connection zone 26 of the second conductive part 22 of the electric-conductive layer 20 to the connecting lines. In an embodiment, the connection wires are further connected to a measuring device (not shown), and the measuring device can display and calculate the ammonia concentration corresponding to the variations of the sensing voltages. Consequently, it can be utilized easily.

Furthermore, in the embodiment, the insulating and waterproof layer 30 can be formed by for example but not limited to insulating and waterproof materials, such as a para-xylene polymer, a screen-printing insulating paste, or a screen printing UV insulating paste. In an embodiment, the insulating and waterproof layer 30 is formed by a screen-printing insulating paste, and dried at for example 60° C. to 140° C. The insulating and waterproof layer 30 partially covers the first conductive part 21 and the second conductive part 22 to make a portion of the first conductive part 21 and a portion of the second conductive part 22 exposed and configured as the first reaction zone 23 and the second reaction zone 24 for being covered by the ammonium ion sensing layer 40 and the pH sensing layer 50, respectively. In an embodiment, the first reaction zone 23 of the first conductive layer 21 and the second reaction zone 24 of the second conductive layer 22 are covered by the ammonium ion sensing layer 40 and the pH sensing layer 50, respectively, insulated and apart from each other, and disposed nearby with a gap so as to facilitate the miniaturization of the sensing electrode 1.

In the embodiment, the ammonium ion sensing layer 40 and the pH sensing layer 50 are formed by for example but not limited to a drop-coating method, a sputtering method, an electrodeposition method or a screen-printing thick-film technique. In the embodiment, the ammonium ion sensing layer 40 formed on the first reaction zone 23 of the first conductive part 21 of the electric-conductive layer 20 is an ammonium ion selective film and its materials can be for example but not limited to an ion carrier, a plasticizer, a heat-resistant resin or the combinations thereof. In an embodiment, the ammonium ion sensing layer 40 further includes a cation exchange agent, and the components of the ammonium ion sensing layer 40 include for example but not limited to an ion carrier with the weight percentage ranged from 0.2 wt. % to 5 wt. %, a plasticizer with the weight percentage ranged from 50 wt. % to 70 wt. %, a heat-resistant resin with the weight percentage ranged from 30 wt. % to 60 wt. % and cation exchange agent with the weight percentage ranged from 0.1 wt. % to 2.5 wt. %. The mixed solution of the ion carrier, the plasticizer, the heat-resistant resin, and the cation exchange agent is dropped on the exposed portion for the ammonium ion sensing layer 40 on the first conductive part 21 of the electric-conductive layer 20 by means of droplet coating. The droplet volume is ranged from 10 μL to 50 μL. Then, it is dried, for example, at 30° C. to 60° C. for 2 to 10 hours and then vacuum dried at, for example, 40° C. to 60° C. for 6 to 18 hours. Consequently, the production of the ammonium ion sensing layer 40 is completed.

On the other hand, the pH sensing layer 50 can be formed by for example but not limited to an electrochemical chronoamperometry (CA) method or an electrochemical cyclic voltammetry (CV) method to deposit an iridium oxide ($IrO_2$) on the exposed second reaction zone 24 of the second conductive part 22 of the electric-conductive layer 20. In an embodiment, the pH sensing layer 50 is formed by the chronoamperometry (CA) method to electroplate the iridium oxide ($IrO_2$) on the exposed second reaction zone 24 of the second conductive part 22 of the electric-conductive layer 20. The current density is ranged from 0.2 mA/cm$^2$ to 5 mA/cm$^2$. In another embodiment, the pH sensing layer 50 is formed by the cyclic voltammetry (CV) method to electroplate the iridium oxide ($IrO_2$) on the exposed second reaction zone 24 of the second conductive part 22 of the electric-conductive layer 20. The working voltage is ranged from −0.2 V to 1.3 V, the scan rate is ranged from 10 mV/s to 100 mV/s and the scan cycle is ranged from 10 times to 100 times. In an embodiment, the deposited pH sensing layer 50 is rinsed by the deionized water to remove the redundant electroplating liquid, and then dried at 80° C. for one hour to remove the redundant water. Consequently, the production of the pH sensing layer 50 is completed. In the embodiment, the electroplating liquid includes for example but not limited to an iridium chloride ($IrCl_x$) with X value of 3 or 4, a hydrogen peroxide with the concentration at 30 wt. %, an oxalic acid, a potassium carbonate with the concentration at 3 M, and a deionized water. The components of the electroplating liquid include the iridium chloride ($IrCl_x$) with the weight percentage ranged from 0.05 wt. % to 0.18 wt. %, the 30 wt. % hydrogen peroxide with the weight percentage ranged from 0.5 wt. % to 1 wt. %, the oxalic acid with the weight percentage ranged from 0.2 wt. % to 0.6 wt. %, the 3M potassium carbonate with the weight percentage ranged from 6 wt. % to 12 wt. %, and the deionized water with the weight percentage ranged from 80 wt. % to 90 wt. %.

In the above embodiments, the pad 60 is disposed around the ammonium ion sensing layer 40 and the pH sensing layer 50, and the interior of the opening 61 of the pad 60 is configured to define an accommodation space for filling with the electrolyte layer 70. In an embodiment, the pad 60 can be formed by for example but not limited to a polyethylene terephthalate (PET) or a poly vinyl chloride (PVC). In an embodiment, the pad 60 is formed by the PET with the thickness of 0.35 mm. The pad 60 has a backside with an adhesive tape, which is attached to the planar surface 11 of the insulating base plate 10 and disposed around the periphery of the ammonium ion sensing layer 40 and the pH sensing layer 50. Then, it is pressed and hold for 12 hours by a rolling machine so as to make it adhered firmly. The interior of the opening 61 of the pad 60 is further configured to define the accommodation space for filling with the electrolyte layer 70.

In the above embodiment, the electrolyte layer 70 is constructed by the materials of the liquid electrolyte, which can be for example but not limited to a hydrochloric acid aqueous solution, a potassium chloride aqueous solution, a potassium hydroxide aqueous solution, a sodium chloride aqueous solution, a phosphate buffer aqueous solution, a tris (hydroxymethyl) aminomethane (Tris) aqueous solution or an ammonium chloride aqueous solution. The concentration of the liquid electrolyte is ranged from 0.01 M to 0.1 M. In an embodiment, the electrolyte layer 70 is constructed by the materials of the solid electrolyte. The solid electrolyte includes a gel material attached with electrolyte. The gel material can be for example but not limited to an agarose, a polyacrylamide, a gelatin or a calcium alginate. In an embodiment, the 0.01 M Tris aqueous solution is dispensed in a fixed dispensing volume of 500 µL by a gel dispenser to fill the interior (the accommodation space for the electrolyte) of the opening 61 of the pad 60. Consequently, the production of the electrolyte layer 70 is completed.

Moreover, in the above embodiments, the gas diffusion layer 80 is constructed by the material for example but not limited to a cellulose acetate, a silicone rubber, a polytetrafluoroethylene (PTFE), a copolymer of fluorinated ethylene propylene (FEP), a polydimethylsiloxane (PDMS), a polyvinyl chloride (PVC), a natural rubber or the combinations thereof. In the embodiment, the thickness of the gas diffusion layer 80 is ranged from 0.1 µm to 30 µm. In an embodiment, the gas diffusion layer 80 is formed by a PTFE film with the thickness of 10 µm. The backside of the PTFE film adhered with the adhesive tape is attached to the pad 60 and covers over the electrolyte layer 70, so that the electrolyte layer 70 is sealed in the opening 61 of the pad 60. Consequently, the sensing electrode 1 of the present invention is completed.

In summary, a planar ammonia selective sensing electrode and a manufacturing method thereof are provided. The planar ammonium ion sensing layer and the planar hydroxide ion sensing layer are disposed on an electric-conductive by a drop-coating method, a sputtering method, an electrodeposition method or a screen-printing thick-film technique, so as to improve the accuracy and reduce the volume of the sensing electrode. In addition, the planar ammonia selective sensing electrode is provided with a high selectivity and sensitivity to be applied in the fields of the medicine, the biochemistry, the chemistry, the agriculture, the environmental and others. For example, it can be applied to monitor the variation of the ammonia and nitrogen concentrations during the planting process of hydroponic plants, the variation of the ammonia and nitrogen concentrations of the human sweat, the water quality of the aquaculture, or the specific biological indicators (e.g. creatinine) by means of combining the specific enzymes. Moreover, the structure is compact, the manufacturing process is simplified, and the cost is reduced, so as to facilitate to achieve the purpose of providing disposable sensing electrodes While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A planar ammonia selective sensing electrode, comprising:
    an insulating base plate including at least one planar surface;
    an electric-conductive layer disposed on the at least one planar surface, wherein the electric-conductive layer includes at least one first conductive part and at least one second conductive part, and the first conductive part and the second conductive part are insulated and apart from each other and configured to form a first reaction zone and a second reaction zone, respectively;
    an ammonium ion sensing layer disposed on the first reaction zone;
    a hydroxide ion sensing layer disposed on the second reaction zone; and
    an electrolyte layer disposed on and covering the ammonium ion sensing layer and the hydroxide ion sensing layer.

2. The planar ammonia selective sensing electrode according to claim 1, further comprising an insulating and waterproof layer disposed on the electric-conductive layer and partially covering the first conductive part and the second conductive part, wherein a portion of the first conductive part and a portion of the second conductive part are exposed and configured as the first reaction zone and the second reaction zone, respectively.

3. The planar ammonia selective sensing electrode according to claim 1, wherein the electric-conductive layer further comprises a working electrode connection zone and a counter electrode connection zone disposed on the first conductive part and the second conductive part and connected to the first reaction zone and the second reaction zone, respectively.

4. The planar ammonia selective sensing electrode according to claim 1, further comprising a pad disposed on the at least one planar surface of the insulating base plate, wherein the pad includes an opening, the pad is disposed around the ammonium ion sensing layer and the hydroxide ion sensing layer, and the electrolyte layer is accommodated in an interior of the opening.

5. The planar ammonia selective sensing electrode according to claim 4, further comprising a gas diffusion layer disposed on the electrolyte layer and attached to the pad for holding the electrolyte layer among the gas diffusion layer, the ammonium ion sensing layer and the hydroxide ion sensing layer.

6. The planar ammonia selective sensing electrode according to claim 1, wherein the hydroxide ion sensing layer is a pH sensing layer.

7. The planar ammonia selective sensing electrode according to claim 1, wherein the first reaction zone and the second reaction zone are located at ends of the first conductive part and the second conductive part, respectively.

8. The planar ammonia selective sensing electrode according to claim 7, wherein the electric-conductive layer further comprises a working electrode connection zone and a counter electrode connection zone disposed on the first conductive part and the second conductive part, respectively, and located at ends opposite to the ends where the first reaction zone and the second reaction zone located at.

9. The planar ammonia selective sensing electrode according to claim 8, further comprising an insulating and waterproof layer disposed on the electric-conductive layer and partially covering the first conductive part and the second conductive part, wherein the first reaction zone and the working electrode connection zone are formed at the two ends of the first conductive part, and the second reaction zone and the counter electrode connection zone are formed at the two ends of the second conductive part.

10. A manufacturing method of a planar ammonia selective sensing electrode, comprising steps of:
(a) providing an insulating base plate including at least one planar surface, and forming an electric-conductive layer on the at least one planar surface of the insulating base plate, wherein the electric-conductive layer includes at least one first conductive part and at least one second conductive part, and the first conductive part and the second conductive part are insulated and apart from each other and configured to form a first reaction zone and a second reaction zone, respectively;
(b) forming an ammonium ion sensing layer on the first reaction zone and a hydroxide ion sensing layer on the second reaction zone, respectively; and
(c) forming an electrolyte layer to cover over the ammonium ion sensing layer and the hydroxide ion sensing layer.

11. The manufacturing method of the planar ammonia selective sensing electrode according to claim 10, wherein the step (b) further comprises a step of (b1) forming an insulating and waterproof layer on the electric-conductive layer and allowing the insulating and waterproof layer to partially cover the first conductive part and the second conductive part, wherein a portion of the first conductive part and a portion of the second conductive part are exposed and configured as the first reaction zone and the second reaction zone, respectively.

12. The manufacturing method of the planar ammonia selective sensing electrode according to claim 11, wherein the first reaction zone and the second reaction zone are located at ends of the first conductive part and the second conductive part, respectively.

13. The manufacturing method of the planar ammonia selective sensing electrode according to claim 12, wherein at the step (b1), a working electrode connection zone and a counter electrode connection zone are formed on the first conductive part and the second conductive part, respectively, and located at ends opposite to the ends where the first reaction zone and the second reaction zone located at.

14. The manufacturing method of the planar ammonia selective sensing electrode according to claim 10, wherein the step (c) further comprises a step of (c1) providing a pad including an opening and placing the pad on the at least one planar surface of the insulating base plate, wherein the pad is disposed around the ammonium ion sensing layer and the hydroxide ion sensing layer, and the electrolyte layer is accommodated in an interior of the opening.

15. The manufacturing method of the planar ammonia selective sensing electrode according to claim 14, further comprising a step of (d) forming a gas diffusion layer on the electrolyte layer and attaching the gas diffusion layer to the pad, so as to hold the electrolyte layer in the interior of the opening.

16. The manufacturing method of the planar ammonia selective sensing electrode according to claim 10, wherein the hydroxide ion sensing layer is a pH sensing layer.

17. The manufacturing method of the planar ammonia selective sensing electrode according to claim 10, wherein at the step (b), the ammonium ion sensing layer and the hydroxide ion sensing layer is formed by a drop-coating method, a sputtering method, an electrodeposition method or a screen-printing thick-film technique.

* * * * *